United States Patent
Koh et al.

(10) Patent No.: US 10,245,268 B2
(45) Date of Patent: Apr. 2, 2019

(54) TREATMENT OF ACVR1-MEDIATED DISEASES

(71) Applicant: Sierra Oncology, Inc., Plymouth, MI (US)

(72) Inventors: Brian Koh, Foster City, CA (US); Igor Theurl, Innsbruck (AT); Matthew Robert Warr, Issaquah, WA (US); James Andrew Whitney, Mercer Island, WA (US)

(73) Assignee: Sierra Oncology, Inc., Plymouth, MI (US)

( * ) Notice: Subject to any disclaimer, the term of this patent is extended or adjusted under 35 U.S.C. 154(b) by 0 days.

(21) Appl. No.: 15/671,978

(22) Filed: Aug. 8, 2017

(65) Prior Publication Data

US 2018/0042933 A1 Feb. 15, 2018

Related U.S. Application Data

(60) Provisional application No. 62/373,161, filed on Aug. 10, 2016.

(51) Int. Cl.
*A61K 31/5377* (2006.01)
*A61K 31/7064* (2006.01)

(52) U.S. Cl.
CPC ...... *A61K 31/5377* (2013.01); *A61K 31/7064* (2013.01)

(58) Field of Classification Search
CPC .................. A61K 31/5377; A61K 31/7064
See application file for complete search history.

(56) References Cited

U.S. PATENT DOCUMENTS

| | | | |
|---|---|---|---|
| 8,486,941 B2 | 7/2013 | Burns et al. | |
| 2009/0253132 A1 | 10/2009 | Kaplan et al. | |
| 2015/0361050 A1 | 12/2015 | Brown et al. | |

FOREIGN PATENT DOCUMENTS

WO WO-2012/071612 A1 6/2012

OTHER PUBLICATIONS

Han et al. ,Bone 2017, pp. 9-10.*
Kitoh et al. ,Orphanet Journal of Rare diseases, 2013, 8 :163 , pp. 1-7.*
Asshoff et al. Blood, 2017, vol. 129(13) , pp. 1823-1830.*
Schafer et al. Drug Discovery Today 2008, 13 (21/22), 913-916.*
Horig et al. Journal of Translational Medicine 2004, 2(44).*
Asshoff, M. et al. (Dec. 7, 2015). "The Jak1/Jak2 Inhibitor Momelotinib Inhibits Alk2, Decreases Hepcidin Production and Ameliorates Anemia of Chronic Disease (ACD) in Rodents," located at <https://ash.confex.com/ash/2015/webprogramscheduler/Paper81585.html>, last visited on Dec. 26, 2017, 2 pages.
Asshoff, M. et al. (2015). "The Jak1/Jak2 Inhibitor Momelotinib Inhibits Alk2, Decreases Hepcidin Production and Ameliorates Anemia of Chronic Disease (ACD) in Rodents," *Blood* 126(23):538, Abstract Only, located at <http://www.bloodjournal.org/content/126/23/538?sso-checked=true>, last visited on Dec. 26, 2017, 4 pages.
Berge, et al. (Jan. 1977). "Pharmaceutical Salts," *Journal of Pharmaceutical Science* 66(1):1-19.
Hino, K. et al. (Dec. 15, 2015). "Neofunction of ACVR1 in Fibrodysplasia Ossificans Progressiva," *PNAS* 112(50):15438-15443.
Shen, Q. et al. (Nov. 2009). "The Fibrodysplasia Ossificans Progressiva R206H ACVR1 Mutation Activates BMP-Independent Chondrogenesis and Zebrafish Embryo Ventralization," *The Journal of Clinical Investigation* 119(11):3462-3472.
Taylor, K. R. et al. (May 2014). "Recurrent Activating ACVR1 Mutations in Diffuse Intrinsic Pontine Glioma," *Nat Genet.* 46(5):457-461.
Warren, K.E. (Dec. 2012). "Diffuse Intrinsic Pontine Glioma: Poised for Progress," *Frontiers in Oncology* 2(205):1-9.
International Search Report dated Nov. 15, 2017, for PCT Patent Application No. PCT/US2017/045957, filed Aug. 8, 2017, 3 pages.
Office Action dated Mar. 8, 2018 for Taiwan Patent Application No. 106126913, filed Aug. 9, 2017, 9 pages. (Includes English translation).
Written Opinion from the International Searching Authority dated Nov. 15, 2017, for PCT Patent Application No. PCT/US2017/045957, filed Aug. 8, 2017, 5 pages.

* cited by examiner

*Primary Examiner* — Savitha M Rao
(74) *Attorney, Agent, or Firm* — Fenwick & West LLP

(57) ABSTRACT

Provided herein are methods, compositions, and kits for treating ACVR-1-mediated diseases using N-(cyanomethyl)-4-[2-4-morpholinoanilino)pyrimidin-4-yl]benzamide.

18 Claims, No Drawings
Specification includes a Sequence Listing.

SEQUENCE LISTING

<160> NUMBER OF SEQ ID NOS: 1

<210> SEQ ID NO 1
<211> LENGTH: 509
<212> TYPE: PRT
<213> ORGANISM: Artificial Sequence
<220> FEATURE:
<223> OTHER INFORMATION: Synethtic ACVR1 polypeptide sequence

<400> SEQUENCE: 1

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

```
Ser Phe Pro Gly Thr Gln Asn Phe His Leu Glu Val Gly Leu Ile Ile
            115                 120                 125

Leu Ser Val Val Phe Ala Val Cys Leu Leu Ala Cys Leu Leu Gly Val
130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
                180                 185                 190

Gly Ser Gly Leu Pro Phe Leu Val Gln Arg Thr Val Ala Arg Gln Ile
                195                 200                 205

Thr Leu Leu Glu Cys Val Gly Lys Gly Arg Tyr Gly Glu Val Trp Arg
            210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
                260                 265                 270

Arg His Ser Ser Thr Gln Leu Trp Leu Ile Thr His Tyr His Glu Met
            275                 280                 285

Gly Ser Leu Tyr Asp Tyr Leu Gln Leu Thr Thr Leu Asp Thr Val Ser
290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
                340                 345                 350

Ala Asp Leu Gly Leu Ala Val Met His Ser Gln Ser Thr Asn Gln Leu
            355                 360                 365

Asp Val Gly Asn Asn Pro Arg Val Gly Thr Lys Arg Tyr Met Ala Pro
370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
                420                 425                 430

Asp Val Val Pro Asn Asp Pro Ser Phe Glu Asp Met Arg Lys Val Val
            435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505
```

TREATMENT OF ACVR1-MEDIATED DISEASES

CROSS REFERENCE TO RELATED APPLICATIONS

This application claims the benefit of U.S. Provisional App. No. 62/373,161, filed Aug. 10, 2016, the entirety of which is hereby incorporated by reference.

SEQUENCE LISTING

The Sequence Listing associated with this application is provided in text format in lieu of a paper copy, and is hereby incorporated by reference into the specification. The name of the text file containing the Sequence Listing is 1158_PC_SEQ_ST25.txt. The text file created on Aug. 3, 2017, is 4.54 KB in size and submitted electronically via EFS-Web.

BACKGROUND

The activin A receptor type-1 (ACVR1) gene encodes a kinase that is a member of the bone morphogenetic protein (BMP) type I receptors included in the TGF-β receptor subfamily. Activins signal through a heteromeric complex of receptor serine kinases that include at least two type I (I and IB) and two type II (II and IIB) receptors. These receptors are transmembrane proteins composed of a ligand-binding extracellular domain having a cysteine-rich region, a transmembrane domain, and a cytoplasmic domain with predicted serine/threonine specificity. Type I and II receptors form a stable complex after ligand binding. Type II receptors phosphorylate and activate type I receptors, which autophosphorylate and then bind and activate SMAD transcriptional regulators.

Mutations in ACVR1 have been identified in fibrodysplasia ossificans progressiva (FOP) that aberrantly activate ACVR1. FOP is a rare genetic disorder of progressive extraskeletal ossification, leading to profoundly decreased mobility of affected individuals. Patients with classic FOP generally have congenital malformation of the great toes and develop progressive heterotopic ossification within soft connective tissues in characteristic anatomic patterns. A gene mutation for patients with the classic FOP clinical phenotype was mapped to chromosome 2q23-24, and mutations were identified in ACVR1.

Activating mutations in ACVR1 have also been identified in diffuse intrapontine gliomas (DIPGs), which are highly aggressive glial neoplasms of the ventral pons that are difficult to treat, generally in the pediatric population. Surgical resection is unsuitable due to the location at the base of the brain and no chemotherapeutic or target agent has been identified as providing substantial survival benefit; radiotherapy is the standard of care and provides palliative benefit.

Thus, there is a need for further therapies that target ACVR1, including mutated forms of ACVR1.

BRIEF SUMMARY

Provided herein are methods, compositions, and kits for treating ACVR1-mediated diseases with momelotinib. In some embodiments, the ACVR1-mediated disease is mediated by a mutant ACVR1 polypeptide. In some embodiments, a mutant ACVR1 polypeptide comprises a substitution mutation. In some embodiments, the mutation is an activating mutation in the glycine-serine rich (GS) domain or in the kinase domain. The activating mutation may be, for example, an R206H substitution. In some embodiments, the activating mutation is a R258G/S, G328E/V/W/R, or G356D substitution. In some embodiments, the mutant ACVR1 polypeptide comprises a R206H, Q207E, R258G/S, G328E/V/W/R, or G356D substitution. In some embodiments, the ACVR1-mediated disease is not anemia. In some embodiments, the ACVR1-mediated disease is selected from the group consisting of fibrodysplasia ossificans progressiva (FOP) and diffuse intrapontine glioma (DIPG).

DETAILED DESCRIPTION

The following description sets forth exemplary methods, compositions, kits and articles of manufacture for treating a subject having an ACVR1-mediated disease with momelotinib. Such description exemplifies embodiments and does not limit the scope of the present disclosure.

The compound N-(cyanomethyl)-4-[2-(4-morpholinoanilino)pyrimidin-4-yl]benzamide, also known as momelotinib, is a Janus-kinase (JAK) inhibitor. Momelotinib competes with JAK1/2 for ATP binding. In clinical studies, it is effective in treating myeloproliferative disorders. Patients having myelofibrosis who received momelotinib also exhibited improvement in anemia and/or spleen responses. Methods of synthesizing momelotinib are described in U.S. Pat. No. 8,486,941, which is incorporated by reference in its entirety. The structure as shown in U.S. Pat, No. 8,486,941 is:

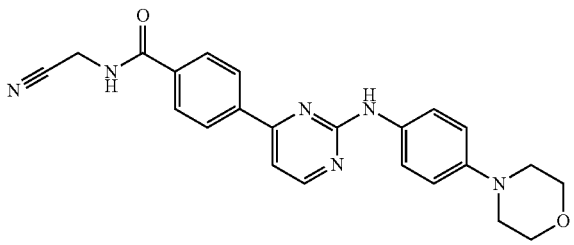 [SMILES: N#CCNC(=O)c1ccc(-c2ccnc(Nc3ccc(N4CCOCC4)cc3)n2)cc1]

Additional forms of momelotinib and methods of preparation are described in U.S. Patent Application Publication No. 2015/0361050 and International Application Publication No. WO 2012/071612, each of which is herein incorporated by reference in its entirety.

"ACVR1" refers to a kinase that is a member of the bone morphogenetic protein (BMP) type I receptors include in the TGF-β receptor subfamily. BMP receptors are heteromeric receptor complexes made up of type I and type II transmembrane serine/threonine kinase receptors. Both the type I and type II receptors have an extracellular ligand binding domain (ECD) and an intracellular serine/threonine kinase domain. Type I receptors also have a glycine/serine-rich region (GS-box) preceding the kinase domain and a L45 loop within the kinase domain. The type I and type II receptors work in concert to activate downstream signaling pathways, such as Smad and non-Smad signaling pathways. Activation involves ligand binding, ligand-receptor oligomerization and transphosphorylation of the GS box of the type I receptor by the type II receptor kinase. The human ACVR1 gene is localized to chromosome 2q24.1 (human genome build GRCh38) and encodes a 509-amino acid polypeptide. The ACVR polypeptide sequence available under UniProte accession number Q04771 is shown in SEQ ID NO:1. ACVR1 is also known as ALK2, ActRIA and Tsk7L. In this disclosure, ACVR1 mutations are described with reference to SEQ ID NO:1. Thus, for example, a R206H mutation refers to substitution in which histidine is substituted for the arginine at position 206 of SEQ ID NO:1.

As used herein, the term "ACVR1-mediated disease" refers to a disease in which ACVR1 plays a role in the pathogenesis of the disease.

Momelotinib can be used to treat any number of ACVR1-mediated diseases, including diseases mediated by mutant ACVR1 proteins. "Treatment" or "treating" as used herein refers to a beneficial effect or desired clinical result. Beneficial effects or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition or delaying the worsening or progression of the disease or condition, and/or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival).

"Prevention" or "preventing" means any treatment of a disease or condition that causes the clinical symptoms of the disease or condition not to develop. Momelotinib may, in some embodiments, be administered to a subject who is at risk or has a family history of an ACVR1-mediated disease in order to prevent development of the disease.

The terms "subject" or "patient" as used herein refers refer to an animal, typically a mammal, e.g., a human. The methods described herein may be useful in human therapy and/or veterinary applications. In some embodiments, the subject is a mammal. For instance, mammals including, but not limited to, cows, sheep, goats, horses, dogs, cats, guinea pigs, rats or other bovine, ovine, equine, canine, feline, rodent or murine species that have an ACVR1-mediated disease can be treated. In one embodiment, the subject is a human. The terms "subject in need thereof" or "patient in need thereof" refer to a subject or a patient who may have, is diagnosed, or is suspected to have an ACVR1-mediated disease that would benefit from the treatment described herein. In certain embodiments, the subject or patient who (i) has not received any treatment, (ii) has received prior treatment and is not responsive or did not exhibit improvement, or (iii) is relapse or resistance to prior treatment. In some embodiments, a subject or patient treated according to the instant disclosure does not have anemia.

ACVR1-mediated Diseases

Disclosed herein are methods of treating ACVR1-mediated diseases comprising administering momelotinib or a pharmaceutically acceptable salt thereof to a patient. In some embodiments, the ACVR1-mediated disease is mediated by a mutant ACVR1 polypeptide. In some embodiments, the ACVR1-mediated disease is fibrodysplasia ossificans progressiva (FOP). In some embodiments, the ACVR1-mediated disease is diffuse intrapontine glioma (DIPG). In some embodiments, the ACVR1-mediated disease is not anemia.

In some embodiments, a patient that has an ACVR1-mediated disorder has a disease or condition in which ACVR1 is mutated resulting in abnormal signal transduction, e.g., a mutation that results in constitutive activation of ACVR1. For example, activating mutations in ACVR1 have been identified in FOP and DIPG. Illustrative ACVR1 mutations that have been identified include amino acid substitutions, such as the substitution of H for R at position 206 of the polypeptide (R206H), mutations at position 258 of the protein, e.g., in which G or S is substituted for R (R258G/S), mutations at position 328, e.g., in which E, V, W, or R is substituted for G, and G356D in which D is substituted for G at position 256 of the polypeptide. Activating mutations may be present in the intracellular glycine and serine-rich (GS) domain of ACVR1, e.g., R206H, or in the kinase domain. Additional ACVR1 mutations include Q207E and R375P. Certain mutations result in small deletions or insertions in the ACVR1 amino acid sequence. For example, a 3 nucleotide deletion in ACVR1 has been observed in which P197 and F198 are replaced with one leucine residue (Pro197, Phe198>Leu).

In some embodiments, momelotinib is administered to a subject, e.g., a human, that has FOP. Heterotopic ossification in FOP begins in childhood and can be induced by trauma, or may occur without warning. The earliest pathological finding in FOP is perivascular lymphocytic infiltration into normal-appearing skeletal muscle, followed by muscle-cell degeneration and highly vascular fibroproliferative soft tissue swelling. The fibroproliferative lesions evolve, through an endochondral process, into mature lamellar bone with marrow elements. Bone formation is episodic and progressive, leading to extra-articular ankylosis of all major joints of the axial and appendicular skeleton. This disorder, although episodic, is cumulative, and results in permanent disability of increasing severity. Ectopic bone formation is usually first evident in early childhood in children aged 2-6 years.

In some embodiments, momelotinib is administered to a subject that has a FOP mutant allele, but has not exhibited overt clinical symptoms relating to ossification. In some embodiments, momelotinib is administered to a patient that has a parent that has FOP.

Beneficial or positive results in a FOP patient treated with momelotinib include reducing, eliminating, ameliorating, inhibiting the worsening of, or delaying at least one sign or symptom of FOP, such as ectopic or heterotopic bone formation or pain and swelling associated with FOP flare-ups.

In some embodiments, momelotinib is administered to a subject, e.g., a human, that has DIPG. DIPG is characterized by highly aggressive and difficult to treat glial tumors that occur in the pons area of the brainstem. DIPG accounts for approximately 10 percent of all childhood central nervous system tumors. Approximately 300 children are diagnosed with DIPG each year. While DIPG is usually diagnosed when children are between the ages of 5 and 9, they can occur at any age in childhood. These tumors occur in boys and girls equally and do not generally appear in adults.

In some embodiments, the DIPG patient has at least one mutant ACVR1 allele in a tumor sample from the patient. In some embodiments, the mutation in the ACVR1 allele results in abnormal activation, e.g., aberrant or constitutive activation, of ACVR1. Beneficial or positive results in a DIPG patient treated with momelotinib include any reducing in tumor size, in the number of tumor cells, or reducing, eliminating, ameliorating, inhibiting the worsening of, or delaying at least one symptom of DIPG, such problems controlling eye movements, facial expressions, speech, chewing, swallowing, or problems with walking and coordination.

Pharmaceutical Compositions and Administration

In some embodiments, momelotinib is administered in a pharmaceutical composition. Thus, provided herein are also pharmaceutical compositions that contain momelotinib or a pharmaceutically acceptable salt or solvate thereof, and one or more pharmaceutically acceptable vehicles selected from carriers, adjuvants, and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., in Remington: The Science and Practice of Pharmacy, 21st Edition, Lippincott Wiliams and Wilkins, Philadelphia, Pa., 2006 and later editions. As used herein, "solvate" is formed by the interaction of a solvent and a compound.

"Pharmaceutically acceptable" or "physiologically acceptable" refer to compounds, salts, compositions, dosage forms and other materials useful in preparing a pharmaceutical composition that is suitable for veterinary or human pharmaceutical use.

"Pharmaceutically acceptable salts" or "physiologically acceptable salts" refer to salts of pharmaceutical compounds that retain the biological effectiveness and properties of the underlying compound, and that are not biologically or otherwise undesirable. There are acid addition salts and base addition salts. Pharmaceutically acceptable acid addition salts may be prepared from inorganic and organic acids. Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. Journal of Pharmaceutical Science, January 1977 vol. 66, No. 1, and other sources. If the compounds described herein are obtained as an acid addition salt, the free base can be obtained by basifying a solution of the acid salt. Thus, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

The term "therapeutically effective amount" of momelotinib or a pharmaceutically acceptable salt or solvate thereof, means an amount sufficient to effect treatment when administered to a subject, to provide a therapeutic benefit such as amelioration of symptoms or slowing of disease progression. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. Administration of momelotinib may decrease the severity of symptoms associated with an ACVR1-mediated disease by at least about 10%, 20%, 30%, 40%, 50%, 60%, 70%, 80%, 90%, 95% or 100% compared to the corresponding one or more symptoms in the same subject prior to treatment or compared to the corresponding symptom in other subjects not receiving such treatment.

The methods provided herein may be used to inhibit the growth, proliferation, or viability of cancer cells, such as DIPG cells or hepatocellular carcinoma cells, or for the treatment of FOP, cells that participate in osteogenesis, e.g., osteoblasts. Proliferation or cell viability may be decreased by at least 10%, at least 20%, at least 30%, at least 40%, at least 50%, at least 60%, at least 70%, at least 80%, or at least 90% compared to cell viability in the diseased cells in the absence of the inhibitors. Any suitable methods, techniques and assays may be used to measure cell viability, including uses of stains, dyes, and/or various polynucleotide or polypeptide biomarkers of cell growth or viability.

The pharmaceutical compositions may be administered in either single or multiple doses. The pharmaceutical composition may be administered by various methods including, for example, rectal, buccal, intranasal and transdermal routes. In certain embodiments, the pharmaceutical compositions may be administered by intra-arterial injection, intravenously, intraperitoneally, parenterally, intramuscularly, subcutaneously, orally, topically, or as an inhalant. In some embodiments, the pharmaceutical composition is administered orally.

One mode for administration is parenteral, for example, by injection. The forms in which the momelotinib may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration is another route for administration of a momelotinib-containing pharmaceutical composition. Administration may be via, for example, capsule or enteric coated tablets. In making the pharmaceutical compositions, the active ingredient is usually diluted by an excipient and/or enclosed within such a carrier that can be in the form of a capsule, sachet, paper or other container.

When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

For preparing solid compositions such as tablets, the principal active ingredient may be mixed with a pharmaceutical excipient to form a solid preformulation composition containing a homogeneous mixture of momelotinib or a pharmaceutically acceptable salt or solvate thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills for administration may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The specific dose level of momelotinib for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. A dosage may, e.g., be expressed as a number of milligrams of a compound of the formula per kilogram of the subject's body weight (mg/kg). Dosages of between about 0.01 and 200 mg/kg may be appropriate. In some embodiments, about 0.01 and 150 mg/kg may be appropriate. In other embodiments a dosage of between 0.05 and 100 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

In the treatment of an identified subject, an appropriate unit dose of the selected drug compound will generally be about 0.01 to 500 mg per kg patient body weight per day which can be administered in single or multiple doses. In some embodiment, the dosage level is about 0.1 to about 250 mg/kg per day; such as about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. Suitable unit doses will typically be in the range from 10 to 500 mgs, such as 50-400 mgs, e.g., 100, 150, 200, 250 or 300 mgs. For oral administration, the compositions are preferably provided in the form of tablets containing 1.0 to 1000 milligrams of the active ingredient, particularly 1, 5, 10, 15, 20, 25, 50, 75, 100, 150, 200, 250, 300, 400, 500, 600, 750, 800, 900, and 1000 milligrams of the active ingredient. In some embodiments, the therapeutic effective amount of momelotinib is 100 mg, 150 mg, 200 mg, 250 mg, or 300 mg. The dosage may be selected, for example to any dose within any of these ranges, for therapeutic efficacy and/or symptomatic adjustment of the dosage to the patient to be treated. In one embodiment, momelotinib is administered orally once or twice daily in a unit tablet dose of 150 mg or 300 mg.

Momelotinib may be administered once, twice, three, or four times daily, using any suitable mode described above. Administration or treatment may also be continued for a number of days; for example, commonly treatment would continue for at least 7 days, 14 days, or 28 days, for one cycle of treatment. Treatment cycles are generally known and are frequently alternated with resting periods of about 1 to 28 days, commonly about 7 days or about 14 days, between cycles. The treatment cycles, in other embodiments, may also be continuous. In some embodiments, momelotinib is administered on a regimen of 1 to 2 times per day, preferably once or twice per day.

Momelotinib may be used in combination with one or more additional therapeutic agent to treat a disease, e.g., FOP or DIPG. The therapeutic agents may be in the forms of compounds, antibodies, polypeptides, or polynucleotides. The therapeutic agent includes, but is not limited to, a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof.

In some embodiments, momelotinib is administered for the treatment of DIPG in combination with radiation therapy, such as proton beam therapy, to inhibit tumor growth.

Momelotinib may be used in combination with bisphosphonate and corticosteroids to treat FOP and/or in combination with iontophoresis with steroids or acetic acid to improve diminished range of motion.

A pharmaceutical composition used for treating an ACVR1-mediated disease comprises momelotinib and at least one pharmaceutically acceptable vehicle is also provided herein. Pharmaceutical compositions described herein can be manufactured using any conventional method, e.g., mixing, dissolving, granulating, dragee-making, levigating, emulsifying, encapsulating, entrapping, melt-spinning, spray-drying, or lyophilizing processes. An optimal pharmaceutical formulation can be determined by one of skill in the art depending on the route of administration and the desired dosage. Such formulations can influence the physical state, stability, rate of in vivo release, and rate of in vivo clearance of the administered agent. Depending on the condition being treated, these pharmaceutical compositions can be formulated and administered systemically or locally.

Pharmaceutical compositions disclosed herein may be formulated to contain suitable pharmaceutically acceptable vehicles, which may include, for example, inert solid diluents and fillers, diluents, including sterile aqueous solution and various organic solvents, permeation enhancers, solubilizers and adjuvants. For example, the pharmaceutical compositions may comprise pharmaceutically acceptable carriers, and optionally can comprise excipients and auxiliaries that facilitate processing of the compound or active ingredient into preparations that can be used pharmaceutically. In another example, the pharmaceutical compositions may comprise pharmaceutically acceptable carriers, and optionally can comprise excipients and auxiliaries that facilitate processing of the compound or the active ingredient into preparations that can be used pharmaceutically. The mode of administration generally determines the nature of the carrier. For example, formulations for parenteral administration can include aqueous solutions of the active compounds in water-soluble form. Carriers suitable for parenteral administration can be selected from among saline, buffered saline, dextrose, water, and other physiologically compatible solutions. In one embodiment, carriers for parenteral administration include physiologically compatible buffers such as Hankss solution, Ringers solution, or physiologically buffered saline. For tissue or cellular administration, penetrants appropriate to the particular barrier to be permeated are used in the formulation. Such penetrants are generally known in the art. For preparations including proteins, the formulation can include stabilizing materials, such as polyols (e.g., sucrose) and/or surfactants (e.g., nonionic surfactants), and the like.

Formulations for parenteral use can include dispersions or suspensions prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions can contain substances that increase the viscosity of the suspension, such as sodium carboxymethylcellulose, sorbitol, dextran, and mixtures thereof. Optionally, the suspension also can contain suitable stabilizers or agents that increase the solubility of the compounds to allow for the preparation of highly concentrated solutions. Aqueous polymers that provide pH-sensitive solubilization and/or sustained release of the active agent also can be used as coatings or matrix structures, e.g., methacrylic polymers. Emulsions, e.g., oil-in-water and water-in-oil dispersions, also can be used, optionally stabilized by an emulsifying agent or dispersant (surface active materials; surfactants). Suspensions can contain suspending agents such as ethoxylated isostearyl alcohols, polyoxyethlyene sorbitol and sorbitan esters, microcrystalline cellulose, aluminum metahydroxide, bentonite, agar-agar, gum tragacanth, and mixtures thereof.

Liposomes containing momelotinib also can be employed for parenteral administration. Liposomes generally are derived from phospholipids or other lipid substances. The compositions in liposome form also can contain other ingredients, such as stabilizers, preservatives, excipients, and the like. Preferred lipids include phospholipids and phosphatidyl cholines (lecithins), both natural and synthetic.

Preparations formulated for oral administration can be in the form of tablets, pills, capsules, cachets, dragees, lozenges, liquids, gels, syrups, slurries, elixirs, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets or dragee cores. Oral formulations can employ liquid carriers similar in type to those described for parenteral use, e.g., buffered aqueous solutions, suspensions, and the like.

Kits

Provided herein are also kits that include momelotinib or a pharmaceutically acceptable salt or solvate thereof, and suitable packaging. In one embodiment, a kit further includes instructions for use. In one aspect, a kit includes a compound of the formulae described herein or a pharmaceutically acceptable salt or solvate thereof, and a label and/or instructions for use of the compounds in the treatment of the indications, including the diseases or conditions, e.g., FOP or DIPG, described herein.

```
ACVR1 polypeptide sequence encode by
ACVR1 gene
                                         (SEQ ID NO: 1)
         10         20         30         40
MVDGVMILPV LIMIALPSPS MEDEKPKVNP KLYMCVCEGL 50         60         70         80
SCGNEDHCEG QQCFSSLSIN DGFHVYQKGC FQVYEQGKMT 90        100        110        120
CKTPPSPGQA VECCQGDWCN RNITAQLPTK GKSFPGTQNF 130        140        150        160
HLEVGLIILS VVFAVCLLAC LLGVALRKFK RRNQERLNPR 170        180        190        200
DVEYGTIEGL ITTNVGDSTL ADLLDHSCTS GSGSGLPFLV 210        220        230        240
QRTVARQITL LECVGKGRYG EVWRGSWQGE NVAVKIFSSR 250        260        270        280
DEKSWFRETE LYNTVMLRHE NILGFIASDM TSRHSSTQLW 290        300        310        320
LITHYHEMGS LYDYLQLTTL DTVSCLRIVL SIASGLAHLH 330        340        350        360
IEIFGTQGKP AIAHRDLKSK NILVKKNGQC CIADLGLAVM 370        380        390        400
HSQSTNQLDV GNNPRVGTKR YMAPEVLDET IQVDCFDSYK 410        420        430        440
RVDIWAFGLV LWEVARRMVS NGIVEDYKPP FYDVVPNDPS 450        460        470        480
FEDMRKVVCV DQQRPNIPNR WFSDPTLTSL AKLMKECWYQ 490        500
NPSARLTALR IKKTLTKIDN SLDKLKTDC
```

---

What is claimed is:

1. A method of treating an ACVR1-mediated disease comprising administering momelotinib or a pharmaceutically acceptable salt or solvate thereof to a patient in need thereof, wherein the ACVR1-mediated disease is selected from the group consisting of fibrodysplasia ossificans progressive (FOP) and diffuse intrapontine glioma (DIPG).

2. The method of claim 1, wherein the ACVR1-mediated disease is mediated by a mutant ACVR1 polypeptide.

3. The method of claim 2, wherein the mutant ACVR1 polypeptide comprises a substitution mutation.

4. The method of claim 2, wherein the mutant ACVR1 polypeptide comprises an activating mutation in the glycine-serine rich (GS) domain or in the kinase domain.

5. The method of claim 4, wherein the activating mutation is in the GS domain.

6. The method of claim 5, wherein the activating mutation is an R206H substitution.

7. The method of claim 4, wherein the activating mutation is in the kinase domain.

8. The method of claim 7, wherein the activating mutation is a R258G/S, G328E/V/W/R, or G356D substitution.

9. The method of claim 8, wherein the activating mutation is a R258G/S substitution.

10. The method of claim 8, wherein the activating mutation is a G328E/V/W/R substitution.

11. The method of claim 8, wherein the activating mutation is a G356D substitution.

12. The method of claim 2, wherein the mutant ACVR1 polypeptide comprises a R206H, Q207E, R258G/S, G328E/V/W/R, or G356D mutation.

13. The method of claim 2, wherein the mutant ACVR1 polypeptide comprises a R206H mutation.

14. The method of claim 2, wherein the mutant ACVR1 polypeptide comprises a Q207E mutation.

15. The method of claim 2, wherein the mutant ACVR1 polypeptide comprises a R258G/S mutation.

16. The method of claim 2, wherein the mutant ACVR1 polypeptide comprises a G328E/V/W/R mutation.

17. The method of claim 2, wherein the mutant ACVR1 polypeptide comprises a G356D mutation.

18. The method of claim 1, wherein the ACVR1-mediated disease is not anemia.

* * * * *